United States Patent [19]

Rubio

[11] Patent Number: 4,497,646
[45] Date of Patent: Feb. 5, 1985

[54] CULTIVATION OF RICE WITH SIMULTANEOUS CONTROL OF WEEDS AND FUNGUS DISEASE

[75] Inventor: Valentin de A. Rubio, Mexicali, Mexico

[73] Assignee: Quinica Orgánica de Mëxico, S.A., Mexico

[21] Appl. No.: 410,386

[22] Filed: Aug. 23, 1982

[51] Int. Cl.$^3$ .................... A01N 37/22; A01N 31/10
[52] U.S. Cl. .................................... 71/3; 71/118; 514/741
[58] Field of Search .................. 71/118, 3; 424/349

[56] References Cited

PUBLICATIONS

Kannaiyan et al. Chem. Abst. vol. 87 (1977) 128605q.
Dvukhsherstou et al. Chem. Abst. vol. 86 (1977) 184393k.
Chem. Abst. 10th Collective Index pp. 5782cs and 5783cs.

*Primary Examiner*—Catherine L. Mills
*Attorney, Agent, or Firm*—Martin P. Hoffman; Jean A. Buttni; Mitchell B. Wasson

[57] ABSTRACT

It is disclosed that the known treatment of rice in cultivation with propanil to kill weeds without harming the growing rice plant can be modified so as to simultaneously eliminate the incidence of rice blast disease (which usually appears at the same time as weed infestation) by simultaneous treatment of the rice in cultivation with a combination of pentachloronitrobenzene and propanil, both applied from aqueous spray based on an emulsifiable concentrate of the material or materials.

9 Claims, No Drawings

CULTIVATION OF RICE WITH SIMULTANEOUS CONTROL OF WEEDS AND FUNGUS DISEASE

This invention relates to the growing or cultivation of the annual grass widely cultivated in warm climates for its seed used as human food—referring, of course, to the cereal, rice, known scientifically as "Oryza sativa". It pertains particularly to a novel method for treating simultaneously the growing rice crop to overcome the disastrous effects of weeds including both monocotyledoneus plants—such as crab grass, foxtail, millet, wheat, ryegrass, wild oats, Johnson grass from seed, etc., and dicotyledoneus plants such as pepper grass, plantain, lambs quarter, chickweed, pigweed, curly dock, purslan, etc., and also, at the same time to overcome the killing effect of the fungus disease commonly known as "rice blast" or Piricularia oryzae caused by the fungus Piricularia oryzae, both of which effects occur are at their peak at substantially the same time, particularly in the warm or hot, wet and humid climates where rice is grown.

BACKGROUND OF THE INVENTION

The rice crop is very important as a source of food particularly in highly populated tropical and sub-tropical areas. Its rank in those areas as the principal staple food is as great as that of wheat in northern and temperate areas. The proportion of rice grown in the United States to the total rice crop is small but is increasing especially in Texas, Mississippi, Louisiana, Alabama and Tennessee.

The effective cultivation of rice has been remarkably enhanced by the discovery, as disclosed in U.S. Pat. No. 3,816,092 of a herbicide or weedicide which is very effective in killing both "monocots" and "dicots" and is therefore an excellent herbicide for many crops, but is also extremely selective and specific insofar as non-phytotoxicity to the rice plant and high phytotoxicity to the various weeds other grasses are concerned.

The herbicide or weedicide disclosed in the aforesaid U.S. patent is chemically 3,4-dichloropropioanilide and can also be named N-(3,4-dichlorophenyl) propionamide. However, it is commonly called by the simple name "propanil" and will be so designated hereinafter.

However, the rice crop in many areas which are not and humid, including southern USA and Mexico, is increasingly endangered, not only by weeds, but also by "rice blast" fungus disease (caused by the fungus Piricularia oryzae) which develops two weeks or so after the rice germinates at the very same time as weeds must be controlled by treatment of the crop with propanil. This poses a very serious problem for the agronomist because of the problems encountered when one attempts to treat the new crops simultaneously with propanil and with a fungicide which is effective against rice blast. Many fungicides for other fungus diseases are not effective against Piricularia oryzae and those that are known to have an effect can not be applied to the rice crop in combination with or at the same time as propanil. There are two distinct reasons for this. The first is the fact that most of the chemicals known to be fungicidal to rice blast are carbamates or organo phosphates combined with the further fact that all these fungicides and similar chemicals inhibit the synthesis of the enzyme, aryl acetilamidase which breaks down propanil to 3,4-dichloro propioanilide which is the mechanism that makes propanil harmless to the rice plant even though killing other plants.

The second principal reason why fungicides known to be effective to control rice blast can not be used in combination with propanil resides in the lack of formulation compatibility as between the materials. It has been found that propanil for weed control in rice is best formulated with aqueous sprays based on an emulsifiable concentrate available commercially from the propanil supplier. If the fungicide desired to be used in combination with propanil so as to control both weeds and rice blast is also preparable in form of, or available as, an emulsifiable concentrate, it is obvious that the desired combined treatment by spraying presents no problems. But this is not otherwise the case. For example, the two commercial fungicides known to be most effective in treating rice blast are the material called "Blasticidin" which is basticidin-S benzylamino benzene sulfonate and the material called "Thiabendazole" which is 2-(4'thiazolyl) benzimidazole, and neither of these is available as or so far as is known, can be formulated into an aqueous spray using an emulsifiable concentrate of this material. Instead, their application is from a formulation based on a wettable powder not suitable to obtain an emulsifiable concentrate.

SUMMARY OF INVENTION

I have now discovered, quite unpredicably, that pentachloronitrobenzene, hereinafter sometimes called PCNB, an easily prepared, economical pesticide having known fungicidal activity, and effective in treating certain fungus diseases, but heretofore unknown to have fungicidal activity against rice blast, can be formulated into aqueous spray from emulsifiable concentrates of PCNB, mixed with similar formulation from emulsifiable concentrate of propanil, either prior to or at the point of application and applied to rice in cultivation to control weeds and rice blast simultaneously. I have found that the PCNB has no effect on the herbicidal activity of propanil or the mechanism of its activity, and that such application of PCNB results in excellent control of "rice blast" fungus disease so that the combined application of the two agents is complementary one to the other and excellent yields of rice grain per unit are secured because of the simultaneous control of both weeds and fungus disease thereby affected.

DETAILED DESCRIPTION OF INVENTION

The invention will be described in detail by reference to typical examples of its practice showing the materials and methods used, and results obtained, in certain controlled field tests and experiments designed to determine the possibility of simultaneous control, with propanil and PCBN, of weeds and rice blast in rice cultivation. Three representative areas, herein designated "A", "B" and "C", where selected for the field tests, all in the area where commercial rice is grown in the State of Campeche, Republic of Mexico. In all representative areas in previous years there existed a very high incidence of weeds and of Piricularia and in some instances, further to insure high incidence of the fungus disease, affected leaves were collected, blended, strained and applied to the experimental area. For purpose of comparison, the results of similar field tests using propanil for weed control in combination with fungicides known to be effective against rice blast for fungus control are also presented.

The areas were also substantially similar, or closely analogous, in terms of soil characteristics, temperature, humidity, rainfall and incidence of weeds and Piricularia to many rice growing areas in the United States in parts of Texas, Mississippi, Louisiana, Alabama and Tennesee, in particular.

The tests and experiments were effected in the area described under conditions of dry land farming, the rice variety used in each case was "Novalto A-71" planted by broadcast seeding at the rate of 100–110 kilograms per hectare (the area units "hectare" are used herein since the measurements were taken in these units. One hectare is equal to 10,000 square meters and is 2.471 acres and hence conversions to acres, more familiar to many readers, is easily accomplished). The soil was fertilized before or at planting with 45 kg. phosphorous pentoxide per hectare from triple superphosphate and 75 kg. nitrogen per hetare from urea.

In the Examples (but not in all the comparative experiments) aqueous spray formulations containing both propanil and the candidate fungicide (PCNB in Examples: others in comparative experiments) were prepared in accordance with well-known practice from an emulsifiable concentrate of each material. The preparation of representative emulsifiable concentrates from propanil is disclosed in U.S. Pat. No. 3,816,092 at column 2 line 42 through column 3 line 12, which disclosure is incorporated herein by reference. Although propanil is a liquid under normal conditions while PCNB is a white powder, PCNB is easily formulated into an aqueous spray using an emulsifiable concentrate of PCNB prepared in an analogous manner (except for the change in chemicals) to the emulsifiable concentrate of propanil as described. Solvents of most importance used in emulsifiable concentrates of PCNB are ketones such as isophorone and mesityl oxide or hydrocarbon solvents particularly aromatics such as xylene or toluene. The emulsifiers are the same as for propanil as incdicated in U.S. Pat. No. 3,816,092 column 2 line 52 to column 3 line 12. Suitable emulsifiable concentrates of propanil containing 35 to 50%, preferably 35%, of propanil are available commercially from Rohm & Haas Company and suitable emulsifiable concentrates containing from 20 to 45%, preferably 24%, of PCNB are available from Quimica Organica de Mexico, S.A., a supplier of PCNB.

Parts and percentages shown in the following Examples, unless otherwise indicated, are by weight.

EXAMPLES 1 TO 3

In these examples an aqueous spray was prepared by tank mixing with water, an emulsifiable concentrate containing 35% propanil and an emulsifiable concentrate containing 24% PCNB. The sprays were piped in a single pipe to the rice field but, if desired, sprays of each ingredient (propanil and PCNB) could be separately piped to the field and applied to the crop simultaneously or consecutively (i.e., substantially simultaneously). In either event, rice field A at 15 days after germination of the rice was sprayed with the spray formulation at the rates per hectare indicated below and 15 days later the rice was sprayed with the same formulation at the rates indicated.

| Example No. | Liters PCNB in 1st spray per hectare | Liters Propanil in 1st spray per hectare | Liters PCNB in 2nd spray per hectare | Liters Propanil in 2nd spray per hectare |
| --- | --- | --- | --- | --- |
| 1 | 1.5 | 5.5 | 1.5 | 6.5 |
| 2 | 5.0 | 5.5 | 5.0 | 6.5 |
| 3 | 10.0 | 5.5 | .0 | 6.5 |

Rice field A was observed 30 days from last application for control of weeds and of rice blast fungus disease. The percentage of control, using the method developed and published by the International Rice Research Institute in the case of the fungus disease in each Example was as follows:

| Example No. | Weed Control | Rice Blast Control |
| --- | --- | --- |
| 1 | 80–100% | 67.4% |
| 2 | 80–100% | 81.6% |
| 3 | 80–100% | 69.8% |

EXAMPLES 4 TO 6

In these examples, rice crops in Areas B & C were treated in the manner described in Examples 1 to 3 for crops in Area A. The control of weeds was found to be equivalent to that stated in Examples 1 to 3. The control of "rice blast" was determined after harvesting of the rice crop in each area. In harvesting, the panicles were cut off, packed and labeled, threshed and the amount of grain determined by weighing the yield at each plot. The figures were converted to metric tons per hectare and are shown as follows:

| parts/ha | | Metric Tons Grain Per Hectare After Treatment with PCNB and Propanil | |
| --- | --- | --- | --- |
| | | Area "B" | Area "C" |
| PCNB | Appl. as in Example 1 | 2.85 | — |
| 5.0 | Appl. as in Example 2 | 3.28 | — |
| 10 | Appl. as in Example 3 | 3.64 | 3.43 |
| | Control no PCNB | 1.15 | 1.43 |

It is to be noted that the yield of rice was more than double by reason of this control of "rice blast" with PCNB, simultaneous with weed control with propanil. It is also to be understood that the rate of application of PCNB may be varied, preferably between 2 and 20 liters/hectare when applied by spray and that two applications of 5–10 liters/hectare are preferable to a single application. The rate of propanil application may also be varied widely as indicated in U.S. Pat. No. 3,816,092. Rates of between 5 and 20 liters of propanil per hectare are exemplary.

It is further to be understood that the above examples are illustrative only and that the specific details may be varied widely without departing from the spirit and scope of the following claims.

Comparative Data on Various Fungicides to Control Rice Blast

In the course of conducting the field tests described in the Examples above, other field tests were conducted to compare the applications against rice blast of various fungicides, (each with propanil weed control) most of which are known to have significant effect when used alone (i.e., without propanil weed control). The following tabulation shows the results of the comparison, including information as to whether the fungicide was used simultaneously with propanil and both formulated from emulsifiable concentrate as desired. The percentage control at optimum concentration is determined as described in Examples 1 to 3.

| Fungicide | Known as useful vs Rice blast | Applied with propanil for weed control both formulated as emulsifiable concentrates | Control at optimum concentration IRM method (Ave) |
|---|---|---|---|
| Blasticidin | yes | no | 83.6% |
| Thiabendazole | yes | no | 75.0% |
| Captan* | yes | yes | 59.7% |
| Etazole* | yes | yes | 44.9% |
| PCNB | no | yes | 81.6% |

*(cis[N(trichloromethylthio)]2-benzinidazole carbamate)
*5-ethoxy-3-trichlormethyl,1,2,4 thiadiazol The advantages of this invention are apparent. PCNB is most effective to control rice blast except for Blasticidin which can not be applied with propanil from emulsifier concentrate and is therefore inoperative in the invention. Further, its cost is 5-10 times that of PCNB.

I claim:

1. A method for simultaneously controlling weed growth and rice blast fungus disease caused by infection of rice plants with *Piricularia oryaze* in cultivated rice fields comprising simultaneously applying to a rice field:
   (a) propanil in the form of an aqueous spray in an amount sufficient to inhibit weed growth but insufficient to damage the rice plants; and
   (b) pentachloronitrobenzene in the form of an aqueous spray in an amount sufficient to inhibit infection of the rice plants with *Piricularia oryzae*.

2. The method according to claim 1 wherein the propanil and the pentachloronitrobenzene are applied together in an aqueous spray composition formulated from each of propanil and pentachloronitrobenzene in the form of an emulsifiable concentrate.

3. The method of claim 2, wherein said aqueous spray composition is applied to a seeded rice field in a single application about 15 days after germination of the rice seeds.

4. The method of claim 2, wherein said aqueous spray composition is applied to a seeded rice field in a first application about 15 days after germination of the rice seeds and in a second application about 15 days after the first application.

5. The method of claim 3, wherein the pentachloronitrobenzene is applied in the single application at a rate equivalent to between 2 and 20 liters of emulsifiable concentrate containing about 24% by weight pentachloronitrobenzene, per hectare.

6. The method of claim 4, wherein the pentachloronitrobenzene is applied in each of the first and second applications at a rate equivalent to between 5 and 10 liters of emulsifiable concentrate containing about 24% by weight pentachloronitrobenzene, per hectare.

7. The method of claim 2, wherein the pentachloronitrobenzene is applied at a rate equivalent to between 2 and 20 liters of emulsifiable concentrate containing about 24% pentachloronitrobenzene per hectare, and the propanil is applied at a rate equivalent to between 5 and 20 liters of emulsifiable concentrate containing about 35% by weight of propanil.

8. The method of claim 4, wherein the pentachloronitrobenzene and the propanil are applied in each of the first and second applications at a rate equivalent to about 5 liters of emulsifiable concentrate containing about 24% by weight pentachloronitrobenzene per hectare and about 5.5 to 6.5 liters of emulsifiable concentrate containing about 35% by weight propanil per hectare.

9. The method of claim 4, wherein the rice field is cultivated under conditions of dry land farming.

* * * * *